(12) United States Patent
Kratz et al.

(10) Patent No.: US 8,642,555 B2
(45) Date of Patent: Feb. 4, 2014

(54) PRODRUGS

(75) Inventors: Felix Kratz, Ehrenkirchen (DE); Andre Warnecke, Freiburg (DE); Bakheet Elsadek, Freibur im Breisgau (DE)

(73) Assignee: KTB Tumorforschungsgesellschaft mbH, Freibur im Breisgau (DE)

( * ) Notice: Subject to any disclaimer, the term of this patent is extended or adjusted under 35 U.S.C. 154(b) by 0 days.

(21) Appl. No.: 13/255,812

(22) PCT Filed: Mar. 9, 2010

(86) PCT No.: PCT/EP2010/001461
§ 371 (c)(1),
(2), (4) Date: Dec. 27, 2011

(87) PCT Pub. No.: WO2010/102788
PCT Pub. Date: Sep. 16, 2010

(65) Prior Publication Data
US 2012/0094892 A1    Apr. 19, 2012

(30) Foreign Application Priority Data
Mar. 9, 2009    (EP) .................................... 09003410

(51) Int. Cl.
*A61K 38/08*    (2006.01)
(52) U.S. Cl.
USPC ......... 514/19.5; 514/1.1; 514/19.2; 514/19.3; 514/21.7; 530/329

(58) Field of Classification Search
None
See application file for complete search history.

(56) References Cited

U.S. PATENT DOCUMENTS

| | | | |
|---|---|---|---|
| 5,208,020 A * | 5/1993 | Chari et al. ................ 424/181.1 |
| 5,948,750 A * | 9/1999 | Garsky et al. ................ 514/19.5 |
| 5,998,362 A | 12/1999 | Feng et al. |
| 2003/0133927 A1 | 7/2003 | DeFeo-Jones et al. |
| 2008/0161245 A1 * | 7/2008 | Kratz et al. ..................... 514/16 |

FOREIGN PATENT DOCUMENTS

| | | |
|---|---|---|
| JP | 2000-509407 A | 7/2000 |
| JP | 2002-510325 A | 4/2002 |
| WO | 98/18493 | 5/1998 |
| WO | 98/18493 A2 | 5/1998 |
| WO | 99/02175 | 1/1999 |
| WO | 99/02175 A1 | 1/1999 |
| WO | 9902175 A1 | 1/1999 |
| WO | 2006/092229 A1 | 9/2006 |
| WO | 2006092229 A1 | 9/2006 |
| WO | WO 2006092229 * | 9/2006 ............. A16K 47/48 |

OTHER PUBLICATIONS

Dubowchik, Gene M. et al; "Cathepsin B-labile dipeptide linkers for lysosomal release of doxorubicin from internalizing immunoconjugates: model studies of enzymatic drug release and antigen specific in vitro anticancer activity." Bioconjugage Chem. (2002) 13(4) p. 855-869.*
Coombs, Gary S. et al; "Substrate specificity of prostate specific antigen (PSA)." Chem. and Biol. (1998) 5 p. 475-488.*
Kratz, et al., "Development of albumin-binding doxorubicin prodrugs that are cleaved by prostate-specific antigen" Archiv Der Pharmazie, VCH Verlagsgesellschaft MBH, Weinheim, DE, vol. 338, No. 10, Oct. 1, 2005, pp. 462-472.
Graeser, et al., "Synthesis and biological evaluation of an albumin binding prodrug of dosorubicin that is cleaved by prostate-specific antigen (PSA) in a PSA-positive orthotopic prostate carcinoma model (LNCaP)", International Journal of Cancer, vol. 122, Oct. 31, 2007, pp. 1145-1154.
Garsky, et al., "The synthesis of a prodrug of doxorubicin designed to provide reduced systemic toxicity and greater target efficacy", Journal of Medicinal Chemistry, American Chemical Society, Washington, US, vol. 44, No. 24, Nov. 22, 2001, pp. 4216-4224.
Brady, et al., "Design and Synthesis of a Pro-Drug of Vinblastine Targeted at Treatment of Prostate Cancer with Enhanced Efficacy and Reduced Systemic Toxicity", Journal of Medicinal Chemistry, vol. 45, Sep. 5, 2002, pp. 4706-4715.
Kumar, et al, "Modulating paclitaxel bioavailability for targeting prostate cancer", Bioorganic & Medicinal Chemistry, Pergamon, vol. 15, No. 14, Jun. 2, 2007, pp. 4973-4987.
International Search Report issued on Jul. 16, 2010 for International Application No. PCT/EP2010/001461.
Office Action dated Aug. 20, 2013 issued in corresponding Japanese Application No. 2011-553344.

* cited by examiner

*Primary Examiner* — Cecilia J Tsang
*Assistant Examiner* — Fred Reynolds
(74) *Attorney, Agent, or Firm* — Knobbe, Martens, Olson & Bear, LLP

(57) ABSTRACT

The present invention relates to a prodrug comprising at least one cytostatic agent, wherein said prodrug is cleavable by prostate-specific antigen (PSA), a process for preparing said prodrug and a pharmaceutical composition containing said prodrug in a pharmaceutically effective amount, for use in the treatment of cancer.

7 Claims, 2 Drawing Sheets

PRODRUGS

RELATED APPLICATIONS

Figure 1:
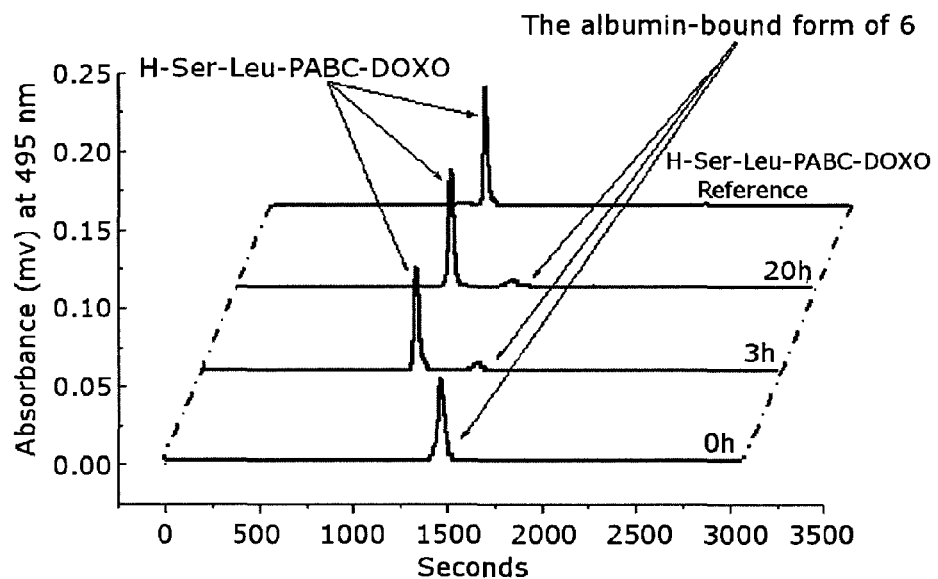

This application is a U.S. National Phase of International Application No. PCT/EP2010/001461, filed Mar. 9, 2010 designating the U.S., and published as WO 2010/102788 on Sep. 16, 2010 which claims the benefit of European Patent Application No. 09003410.9 filed Mar. 9, 2009.

The present invention relates to a prodrug comprising at least one cytostatic agent, wherein said prodrug is cleavable by prostate-specific antigen (PSA), a process for preparing said prodrug and a pharmaceutical composition containing said prodrug in a pharmaceutically effective amount, for use in the treatment of cancer.

Most of the drugs used at present are compounds having low-molecular weights and exhibit, when systemically administered to a patient, a high plasma clearance or total body clearance. Furthermore, said low-molecular weight compounds show a high tendency to penetrate body tissues by diffusion, resulting in a uniform biodistribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytostatic agents.

Several strategies have been pursued for improving the selectivity of low-molecular weight drugs and thus to increase the concentration of the active agent in the desired tissue, while the concentration of the same is decreased in healthy tissues in order to reduce side-effects.

Macromolecular carriers, such as for example albumin, or its drug conjugates exhibit a markedly long half-life in the systemic circulation of up to 19 days (cf. Peters, T. J., "Serum Albumin", *Adv. Protein. Chem.*, 1985, 37, 161-245). Because of an elevated permeability of vessel walls of the e.g. malignant, infected or inflamed tissue for macromolecules, the carrier, such as for example serum albumin, passes preferentially into the target tissue thus achieving a so-called passive targeting effect (cf. Maeda, H., Matsumura, Y., *Crit. Rev. Ther. Drug Carrier Sys.*, 1989, 6, 193-210). The drugs can be bound to exogenous or endogenous albumin (DE 103 10 082 A1, DE 10 2005 009 084 A1).

A macromolecular prodrug strategy for improved cancer chemotherapy has been reported recently (WO 2006/092229). Said strategy is based on two features: (i) rapid and selective binding of thiol-reactive prodrugs to the cysteine-34 position of endogenous albumin after intravenous administration, and (ii) enzymatic release of the albumin bound drug at the tumor site. The prostate-specific antigen (PSA) is a serine protease that is over-expressed in prostate carcinoma and represents a molecular target for selectively releasing an anticancer agent from a prodrug formulation. Further, it has been shown that an albumin-binding derivative of doxorubicin incorporating the peptide sequences Arg-Ser-Ser-Tyr-Tyr-Ser-Arg was efficiently cleaved by PSA releasing the doxorubicin-dipeptide Ser-Arg-DOXO, but further liberation of free doxorubicin from this dipeptide proceeded slowly with a half-live of >48 h. Moreover, although the prodrug was superior over doxorubicin in an orthotopic PSA-positive model, the prodrug was not able to induce tumor remissions (Graeser et al., *Int. J. Cancer*, 2008, 122, 145).

Therefore, a need exists to overcome the above-mentioned problems and to provide prodrugs which enable a faster release of the final cytostatic agent at the desired site of action.

Thus, the technical problem underlying the present invention is to provide novel prodrugs for the treatment of cancer which should exhibit a more efficient release of the free cytostatic agent upon enzymatic cleavage at the desired site of action.

The above technical problem is solved by providing the embodiments characterized in the claims. In particular, according to one aspect of the present invention, there is provided a prodrug having the following formula I:

$$R\text{-}A_n\text{-}Ser\text{-}Leu\text{-}Y\text{—}Z \qquad (I)$$

wherein

R=a protein binding moiety; H; an unsubstituted or substituted residue selected from the group consisting of $C_{1-10}$ alkyl, $C_{1-10}$ alkenyl, $C_{1-10}$ alkynyl and $C_{1-10}$ acyl, wherein the residue may be cyclic, branched or linear, optionally containing one or more heteroatoms; or an unsubstituted or substituted residue selected from the group consisting of aryl, aralkyl and heteroaryl;

A=a peptide sequence consisting of L- and/or D-amino acids, wherein the amino acid residues may be the same or different;

n=an integer from 1 to 10, preferably 1 to 8, more preferably 1 to 6, most preferably 1 to 4, for example 2, 3, 4, 5 or 6, indicating the number of amino acids in the peptide sequence;

Y=a linker moiety; and

Z=a cytostatic agent;

wherein R may be linked to $A_n$ via the terminal $NH_2$ group of the peptide backbone, and Y may be linked to Leu via the COOH group of the α-C-atom.

The term "prodrug" as used herein is not especially restricted as long as the above-defined formula (I) is satisfied. In particular, the term "prodrug" means any form of a drug (or compound) which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part (particularly the cytostatic agent) of the prodrug at the site of action.

The expression "protein-binding moiety" used herein is not specifically restricted and means any functional group which is capable of binding to an amino, a hydroxy or thiol group of a compound which may be of endogenous or exogenous origin. Preferred examples of protein-binding moieties according to the present invention are a maleimide group, a halogenacetamide group, a halogenacetate group, a pyridylthio group, a vinylcarbonyl group, an aziridine group, a disulfide group, a substituted or unsubstituted acetylene group, a hydroxysuccinimide ester group. The protein-binding moiety also includes functional groups, such as —COOH or $SO_3H$, that can be activated by standard coupling agents, e.g. dicyclocarbodiimides, acid chlorides, or peptide coupling reagents (e.g., BOP, HATU, PyBOP). In a preferred embodiment of the present invention the protein-binding moiety is the maleimide group.

One or several prodrugs can be bound to any suitable carrier such as peptides, sugars, serum proteins, antibodies or antibody fragments, growth factors, polysaccharides, or synthetic polymers. The carrier in general may contain suitable functional groups such as hydroxy, amino or thiol groups to bind the protein-binding prodrug. If necessary, these can be introduced in the carrier molecule by chemical modification through techniques known to those skilled in the art (Kratz et al., (2001): Anticancer drug conjugates with macromolecular carriers, in Polymeric Biomaterials, second edition, ed. S. Dumitriu, Marcel Dekker, N.Y., Chapter 32, 851-894).

In a preferred embodiment, the protein-binding moiety of the prodrug according to the present invention allows said prodrug to bind in situ after administration by e.g. injection, to components of body fluids and/or tissue components, preferably to serum proteins and more preferably to serum albumin, particularly to cysteine-34 of serum albumin, and are then present as macromolecular prodrugs which carry the pharmaceutically active compounds to the target site.

According to the present invention, the term "in situ" includes the binding of the prodrug according to the present invention to an endogenous biomolecule, such as a serum protein, particularly serum albumin, inside the organism to which the prodrug has been administered.

A preferred embodiment of the present invention relates to a prodrug as defined above, wherein the residue as defined for R (not including the protein-binding moiety and H), such as $C_{1-10}$ acyl, for example a caproic acid group, is substituted by a protein-binding moiety as defined above, such as a maleimide group. An example of R according to this embodiment of the present invention is ε-maleimidocaproic acid (EMC).

According to a further embodiment of the present invention, R such as $C_{1-10}$ acyl, for example a caproic acid group, is substituted by a moiety, said moiety either lacking protein-binding properties such as a thiol-binding group, or having protein-binding properties such as a thiol-binding group, for example a maleimide group, but said protein-binding properties are blocked/derivatized by substituents such as cysteine. An example of R according to this embodiment is shown below:

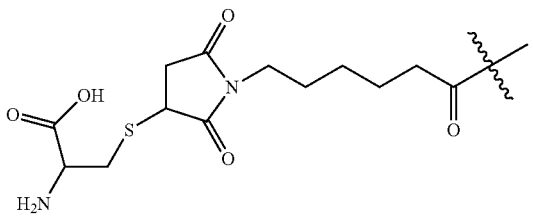 [SMILES: *C(=O)CCCCCN1C(=O)CC(SCC(N)C(=O)O)C1=O]

A preferred embodiment of the present invention relates to the prodrug as defined above, wherein the amino acids in the peptide sequence are selected from the group consisting of Arg, Asn, Gln, Gly, Phe, Ser, Val, Ile, Leu, His, Lys, Ala and Tyr. In a preferred embodiment of the above-defined prodrug the peptide sequence is selected from the group consisting of Arg-Ser-Ser-Tyr-Tyr (SEQ ID NO. 1), Arg-Ser-Ser-Tyr-Ser (SEQ ID NO. 2), Arg-Ser-Ser-Tyr-Arg (SEQ ID NO. 3), Ser-Ser-Tyr-Arg (SEQ ID NO. 4), Ser-Ser-Tyr-Tyr (SEQ ID NO. 5), Arg-Arg-Leu-His-Tyr (SEQ ID NO. 6), Arg-Arg-Leu-Asn-Tyr (SEQ ID NO. 7), Ser-Ser-Lys-Leu-Gln (SEQ ID NO. 8) and Arg-Ala-Ser-Tyr-Gln (SEQ ID NO. 9).

The cytostatic agent Z as defined in the prodrug of the present invention is not specifically restricted and may be selected from the group consisting of N-nitrosoureas, anthracyclines, alkylating agents, antimetabolites, folic acid antagonists, camptothecins, Vinca alkaloids, taxanes, calicheamicins, maytansinoids, auristatins, epothilones, bleomycin, dactinomycin, plicamycin, mitomycin C and cis-configured platinum(II) complexes. Examples of suitable cytostatic agents according to the present invention include the N-nitrosourea nimustine, and any derivatives thereof; the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites, for example purine antagonists or pyrimidin antagonists, 5-fluorouracil, 2'-deoxy-5-fluorouridine, cytarabine, cladribine, fludarabine, pentostatine, gemcitabine and thioguanine, and any derivatives thereof; the folic acid antagonists methotrexate, or raltitrexed, pemetrexed or plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof.

The expression "linker moiety" as used herein includes any group which can bind at least two residues, thus chemically linking said residues together. The "linker moiety" of the present invention is therefore not restricted and can be any chemical moiety which is suitable to bind both a terminal COOH-group of the α-C-atom of Leu and the cytostatic agent Z according to the above-defined formula (I). According to a preferred embodiment of the present invention the linker moiety Y of the above defined prodrug is selected from the group consisting of p-aminobenzyloxycarbonyl (PABC), o-aminobenzyloxycarbonyl, N-methyldiamino ethylene or symmetric N,N'-dimethyldiamino ethylene, a trimethyl lock lactonization linker, and a vinylologous benzyl elimination linker.

The cleavable linker may also contain one or more self-immolative linkers that after peptide cleavage produce (labile) self-immolative spacer drug derivatives that in turn hydrolyse in a spontaneous reaction and release the pharmaceutically and/or diagnostically active compound. One example of a self-immolative linker is a p-aminobenzyloxycarbonyl (PABC) spacer or any of the following, wherein R is a functional group selected from H, Cl, Br, I, F, $NO_2$, CN, OH or an aliphatic or aromatic moiety and the trigger is a peptide that acts as a protease substrate. Specific examples of such a linker are listed in the following Table 1:

TABLE 1

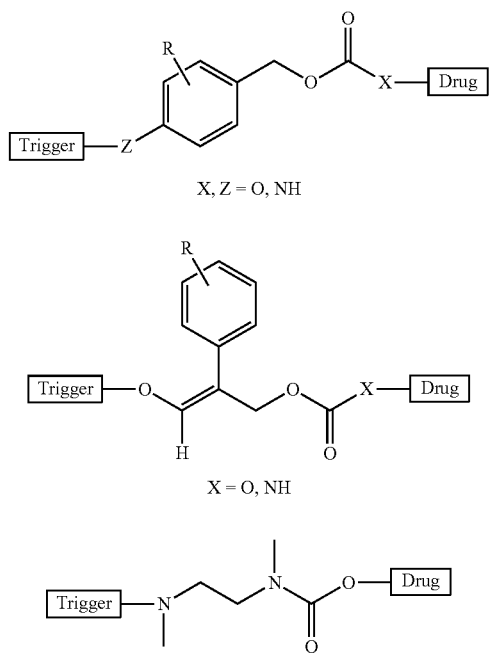

TABLE 1-continued
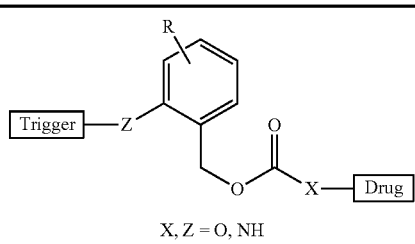
X, Z = O, NH
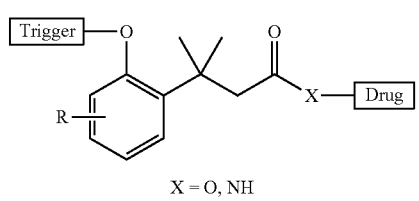
X = O, NH
TABLE 1-continued
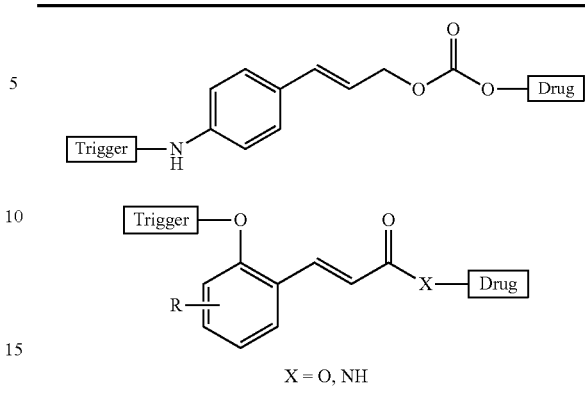
X = O, NH
Examples of the prodrug according to specific embodiments of the present invention are shown below:
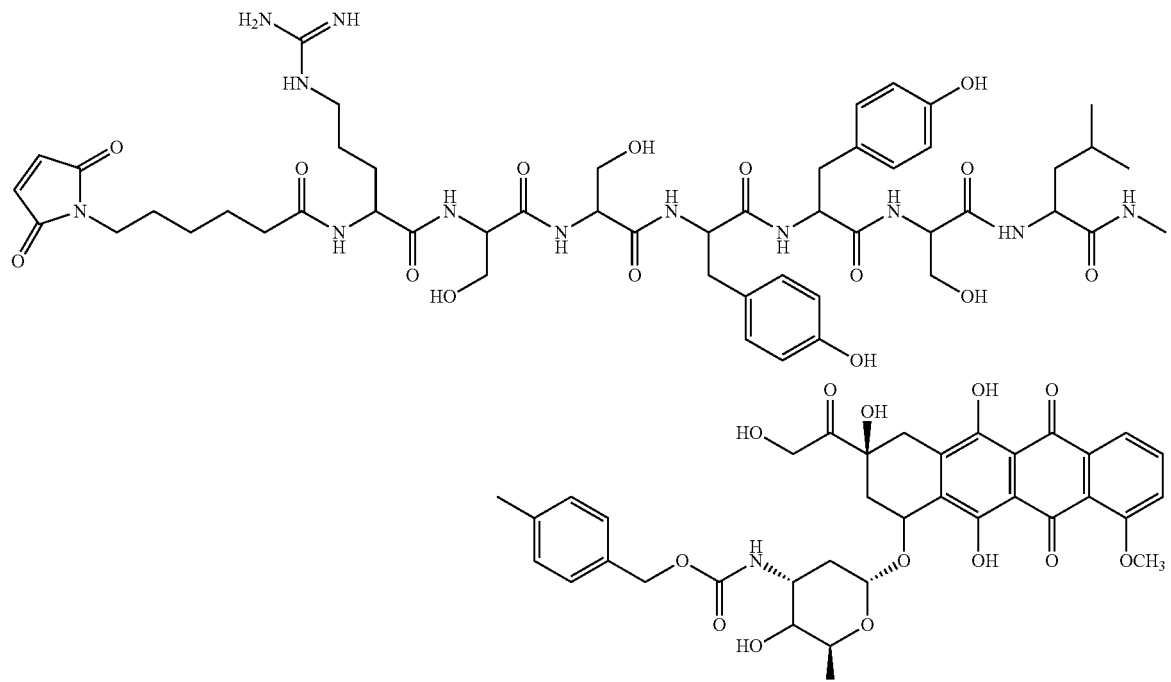
6
(═EMC-Arg-Ser-Ser-Tyr-Tyr-Ser-Leu-PABC-doxorubicin)
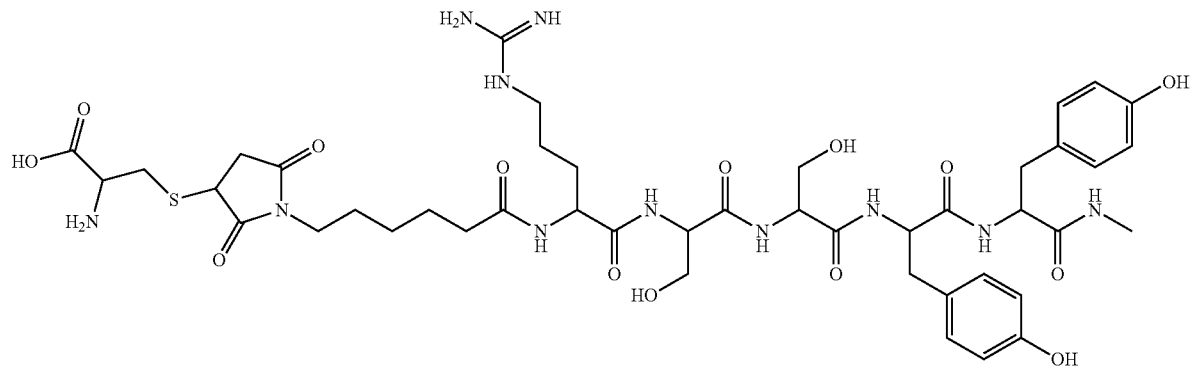

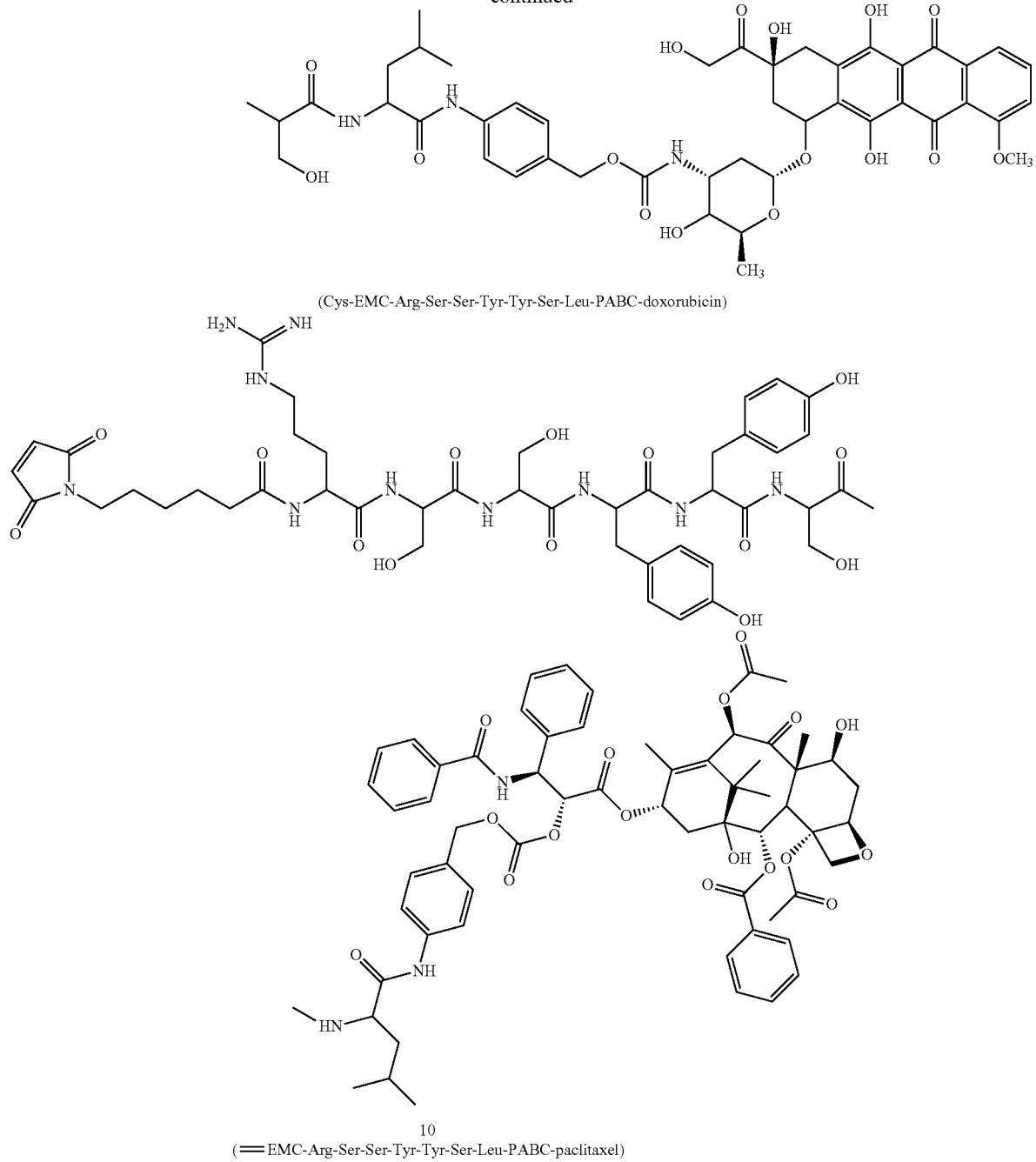

(Cys-EMC-Arg-Ser-Ser-Tyr-Tyr-Ser-Leu-PABC-doxorubicin)

10
(≡EMC-Arg-Ser-Ser-Tyr-Tyr-Ser-Leu-PABC-paclitaxel)

According to a further aspect of the present invention, there is provided a process for the preparation of a prodrug as defined above, comprising the step of reacting a compound having the formula II R-A$_n$  (II)

with a compound having the formula III

Ser-Leu-Y—Z  (III)

wherein R, A, n, Y, and Z are as defined above.

Another aspect of the present invention relates to a pharmaceutical composition containing the above-defined prodrug, and optionally a pharmaceutically acceptable carrier and/or diluent and/or adjuvant. In particular, the pharmaceutical composition may, for example, contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablet or a capsule, or as a composition for inhalation. Particularly, the above-defined pharmaceutical composition is for use in the treatment of cancer.

The figures show:

FIG. 1 displays HPLC-monitored cleavage studies of the albumin-bound form of compound 6 by PSA (20 mg/mL).

Figure 2:
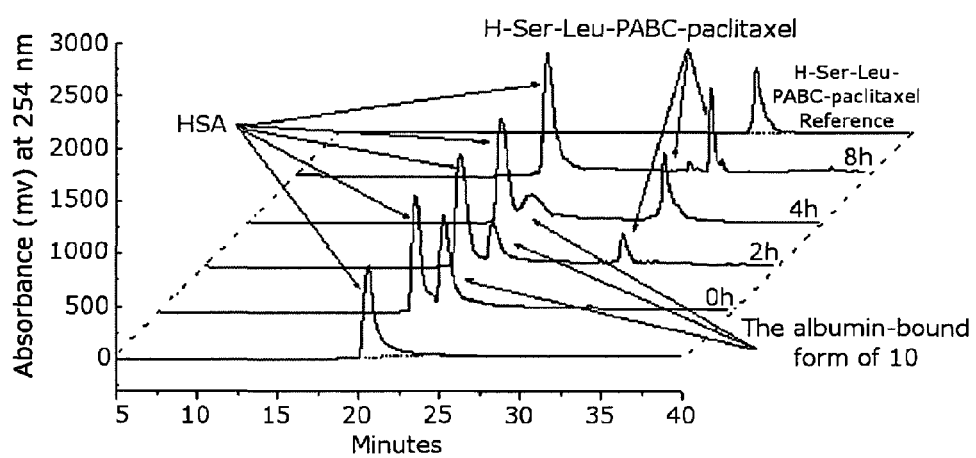

FIG. 2 displays HPLC-monitored cleavage studies of the albumin-bound form of compound 10 by PSA (20 mg/mL).

Figure 3:
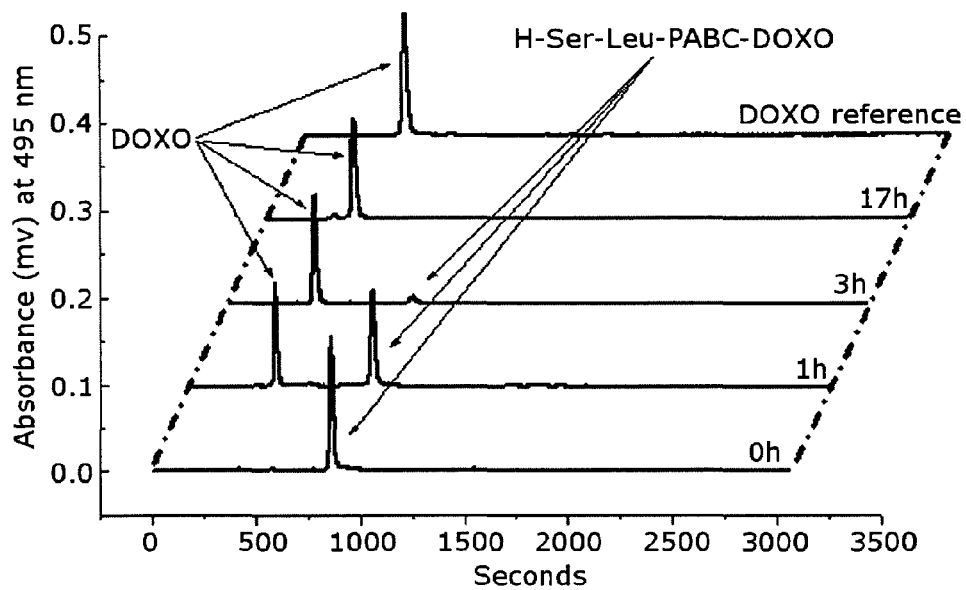

FIG. 3 displays HPLC-monitored cleavage studies of compound 5 by LNCaP prostate tumor tissue homogenates.

Figure 4:
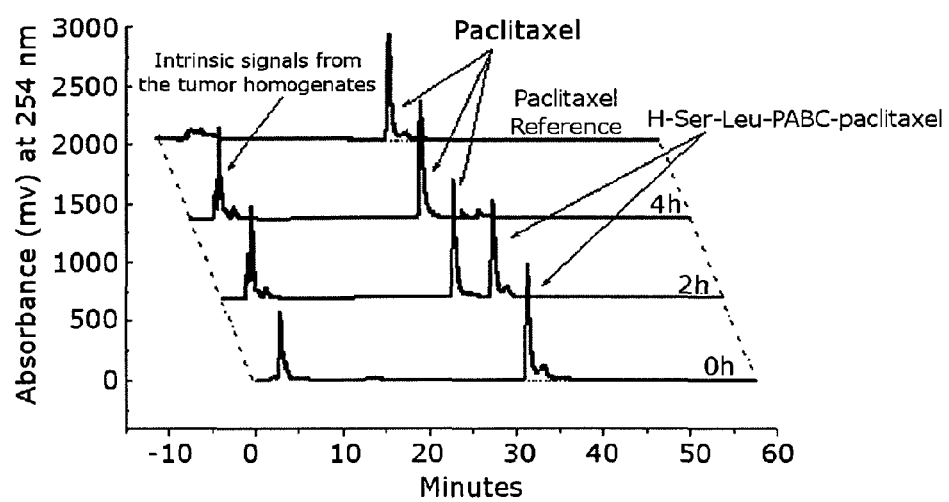

FIG. 4 displays HPLC-monitored cleavage studies of compound 12 by LNCaP prostate tumor tissue homogenates.

The present invention provides novel prodrugs which advantageously show surprisingly an accelerated release of the cytostatic agent contained therein, when the prodrug is enzymatically cleaved preferably at the desired site of action. In particular, the prodrugs of the present invention show optimized release characteristics upon PSA cleavage. These prodrugs of the general formula R-A$_n$-Ser-Leu-Y—Z, for example EMC-Arg-Ser-Ser-Tyr-Tyr-Ser-Leu-PABC-doxorubicin and EMC-Arg-Ser-Ser-Tyr-Tyr-Ser-Leu-PABC-paclitaxel, exhibit excellent water-solubility and may be, for example, bound rapidly to the cysteine-34 position of endogenous and exogenous albumin. Upon cleavage by PSA the dipeptide Ser-Leu-Y—Z is released. Surprisingly, this dipeptide is rapidly degraded to liberate the free cytostatic agent Z, such as doxorubicin and paclitaxel, within a few hours as shown, for example, in LNCaP tumor homogenates. Therefore, a highly improved drug release is advantageously achieved, which is connected to a surprisingly higher efficacy of cytostatic treatment when compared to the state of the art.

The present invention is illustrated in the following examples without any limitation thereto.

EXAMPLES

HPLC Systems
Method A:

Unless otherwise indicated, analytical reversed-phase HPLC of all compounds was carried out on a Kontron system using a solvent delivery system (HPLC Pump 422), a variable wavelength UV-VIS detector (HPLC Detector 430) and a Nucleosil® C-18 column (100-5, 250×4 mm, Macherey-Nagel). For peak integration, Geminyx software (v 1.91 by Goebel Instrumentelle Analytik, FRG) was used. HPLC conditions: flow rate: 1 mL/min, gradient: 0-5 min 100% mobile phase A; 5-35 min increase to 100% mobile phase B; 35-40 min 100% mobile phase B; 40-45 min decrease to 100% mobile phase A; 45-50 min 100% mobile phase A; mobile phase A: 30% CH$_3$CN, 70% water+0.1% TFA, mobile phase B: 70% CH$_3$CN, 30% water+0.1% TFA, injection volume: 50 µL.

Method B:

HPLC for the cleavage, binding and stability studies of the doxorubicin model was performed using a BioLogic Duo-Flow System from Biorad (Munich, Germany) which was connected with a Merck F-1050 fluorescence spectrophotometer (EX. 490 nm, EM. 540 nm) and a Lambda 1000 visible monitor from Bischoff (ë=495 nm); UV-detection at 254 nm; column: Waters, 300 Å, Symmetry C18 5 µm [4.6×250 mm] with pre-column; chromatographic conditions: flow: 1 mL/min, mobile phase A (30% CH$_3$CN, 70% water+0.1% TFA), mobile phase B (50% CH$_3$CN, 50% water+0.1% TFA), gradient: 0-5 min 100% mobile phase A; 5-35 min increase to 100% mobile phase B; 35-40 min 100% mobile phase B; 40-45 min decrease to 100% mobile phase A; 45-50 min 100% mobile phase A; injection volume: 50 µL.

Method C:

HPLC for the cleavage, binding and stability studies of the paclitaxel model was performed using a Kontron system using a solvent delivery system (HPLC Pump 422), a variable wavelength UV-VIS detector (HPLC Detector 430) and a Waters, 300 Å, Symmetry C18 5 µm [4.6×250 mm] column with pre-column. For peak integration, Geminyx software (v 1.91 by Goebel Instrumentelle Analytik, FRG) was used. HPLC conditions: flow rate: 1 mL/min, gradient: 0-5 min 100% mobile phase A; 5-35 min increase to 100% mobile phase B; 35-40 min 100% mobile phase B; 40-45 min decrease to 100% mobile phase A; 45-50 min 100% mobile phase A; mobile phase A: 30% CH$_3$CN, 70% water+0.1% TFA, mobile phase B: 70% CH$_3$CN, 30% water+0.1% TFA, injection volume: 50 µL.

Chemical Synthesis of the Doxorubicin Prodrug

Synthesis of Fmoc-Leu-PABOH (1)

Fmoc-Leu-OH (2.50 g, 7.07 mmol) and N-ethoxycarbonyl-2-ethoxy-1,2-dihydroquinoline (EEDQ) (1.90 g, 7.78 mmol) were dissolved in anhydrous dichloromethane (DCM) (150 mL). After stirring at room temperature for 5 minutes, 4-aminobenzylalcohol (PABOH) (0.95 g, 7.78 mmol) was added and stirring was continued for 24 hours. DCM was then removed under reduced pressure and the product was purified on a silica gel column using chloroform/methanol (50:1) to afford 1 (3.00 g, 92%) as a white powder. APCI-MS (5 uA, MeCN): m/z (%)=459.0 (100) [M+H]$^+$; HPLC (220 nm): >95%.

Synthesis of H-Leu-PABOH (2)

1 (2.50 g, 5.45 mmol) was treated with a solution of 20% piperidine in N,N-dimethylformamide (DMF) (5 mL) and the reaction was stirred for 10 minutes at room temperature. The product was then precipitated with diethyl ether (500 mL), washed three times with diethyl ether and dried in vacuum to afford 2 (1.00 g, 77%) as a white powder. APCI-MS (5 uA, MeCN): m/z (%)=237.1 (100) [M+H]$^+$; HPLC (220 nm): >95%.

Synthesis of Fmoc-Ser(Trt)-Leu-PABOH (3)

Fmoc-Ser(Trt)-OH (1.69 g, 2.96 mmol) and N-hydroxysuccinimide (NHS) (0.34 g, 2.96 mmol) were dissolved in anhydrous DCM (100 mL) and stirred at 0° C. for 10 minutes. Dicyclohexylcarbodiimide (DCC) (0.61 g, 2.96 mmol) was then added and the reaction was stirred at 5° C. for 16 hours. The formed precipitate was filtered off, 2 (0.70 g, 2.96 mmol) and triethylamine (TEA) (0.41 µL, 0.29 g, 2.96 mmol) were then added to the filtrate. After stirring at room temperature for 4 hours, the volatiles were removed under reduced pressure, and the product was crystallized from ethyl acetate/hexane to afford 3 (1.85 g, 79%) as a white powder. APCI-MS (5 uA, MeCN): m/z (%)=788.2 (100) [M+H]$^+$; HPLC (220 nm): >95%.

Synthesis of Fmoc-Ser(Trt)-Leu-PABC-PNP (4)

To a solution of 3 (1.80 g, 2.28 mmol) and bis(p-nitrophenyl) carbonate (2.77 g, 9.12 mmol) in anhydrous DCM (50 mL), N,N-diisopropylethylamine (DIEA) (1163 μL, 0.88 g, 6.84 mmol) was added at 0° C. and the reaction was stirred at room temperature for 48 hours. Subsequently, the volatiles were removed under reduced pressure, and the residue was purified on a silica gel column using chloroform/methanol (100:1) to afford 4 (1.70 g, 78%) as a white powder. ESI-MS (5 kV, MeOH): m/z (%)=975.2 (100) [M+Na]$^+$; HPLC (220 nm): >95%.

Synthesis of H-Ser-Leu-PABC-DOXO (5)

To a solution of 4 (0.75 g, 0.786 mmol) in anhydrous DMF (10 mL), doxorubicin hydrochloride (0.43 g, 0.78 mmol) and DIEA (134 μL, 0.1 g, 0.786 mmol) were added and the reaction was stirred at room temperature for 48 hours. Afterward, the Fmoc protective group was removed by diethylamine (1.5 mL) and the reaction was stirred at room temperature for 10 minutes. The red product was precipitated by diethyl ether (500 mL), washed three times with diethyl ether and dried in vacuum to afford H-Ser(Trt)-Leu-PABC-DOXO (750 mg, 85%).

Subsequently, the Trt protective group was cleaved by dissolving H-Ser(Trt)-Leu-PABC-DOXO (0.30 g, 0.26 mmol) in anhydrous DCM (15 mL) and a solution of 1% TFA in DCM (9 mL) was added dropwise during 15 minutes. After stirring at room temperature for 1 hour, the formed precipitate was purified on a silica gel column using chloroform/methanol (20:1) to afford 5 (190 mg, 80%) as a red powder. ESI-MS (5 kV, MeCN): m/z (%)=915.3 (100) [M+Na]$^+$; HPLC (495 nm): >95%.

Synthesis of EMC-Arg-Ser-Ser-Tyr-Tyr-Ser-Leu-PABC-DOXO (6)

In anhydrous DMF (10 mL) EMC-Arg-Ser-Ser-Tyr-Tyr-OH (107 mg, 0.12 mmol), 5 (100 mg, 0.11 mmol), N-hydroxybenzotriazole (HOBt) (22 mg, 0.33 mmol) and 4-methylmorpholine (48 μL, 44 mg, 0.44 mmol) were dissolved. After stirring for 15 minutes at 0° C., N,N'-diisopropylcarbodiimide (DIPC) (116 μL, 83 mg, 0.66 mmol) was added and the reaction was stirred at 5° C. for 72 hours. The final product was precipitated with diethyl ether (500 mL) and purified on a reverse-phase column using CH$_3$CN/water (40:60)+0.1% TFA to afford 6 (140 mg, 73%) as a red powder after lyophilizing the combined fractions containing the pure product. ESI-MS (5 kV, MeCN): m/z (%)=1742.7 (100) [M+H]$^+$; HPLC (495 nm): >95%.

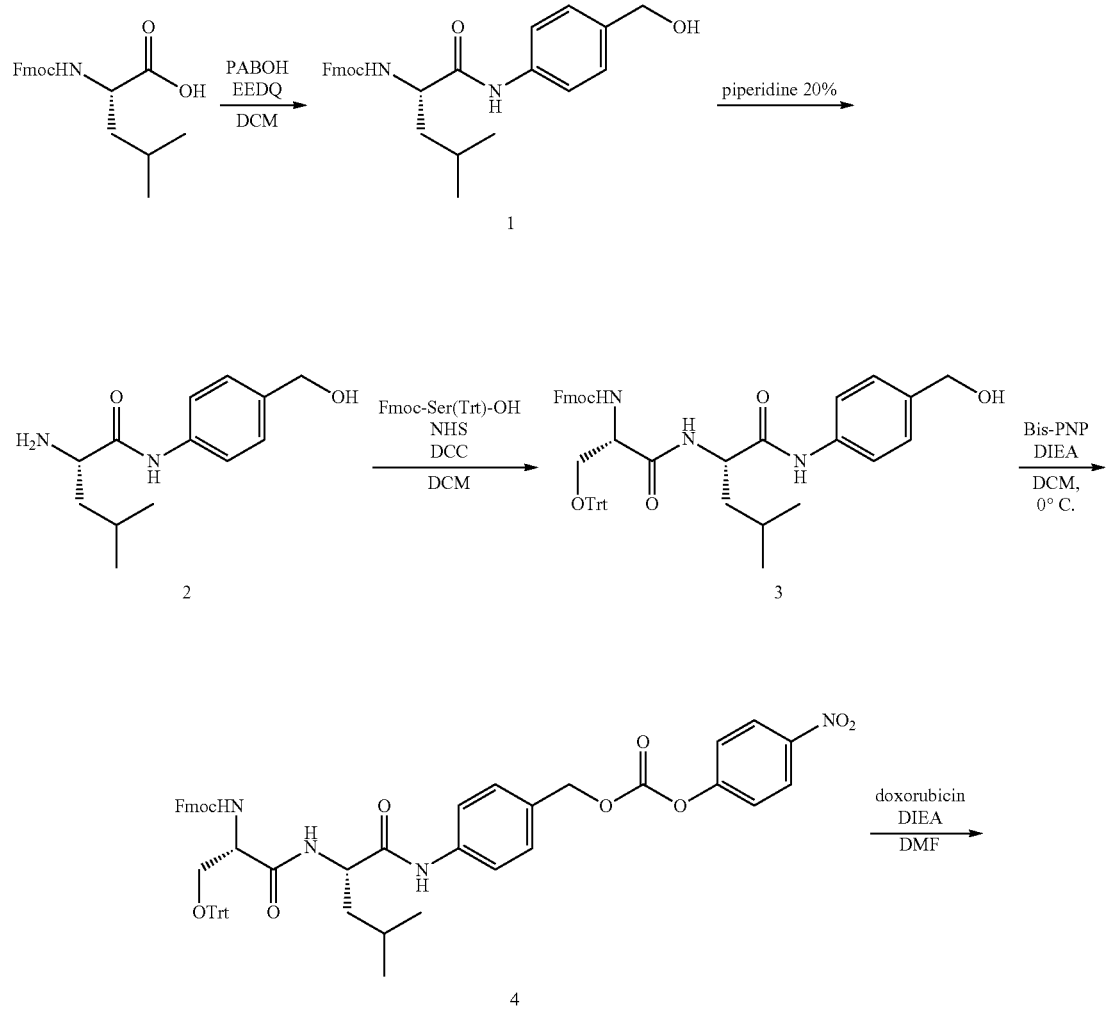

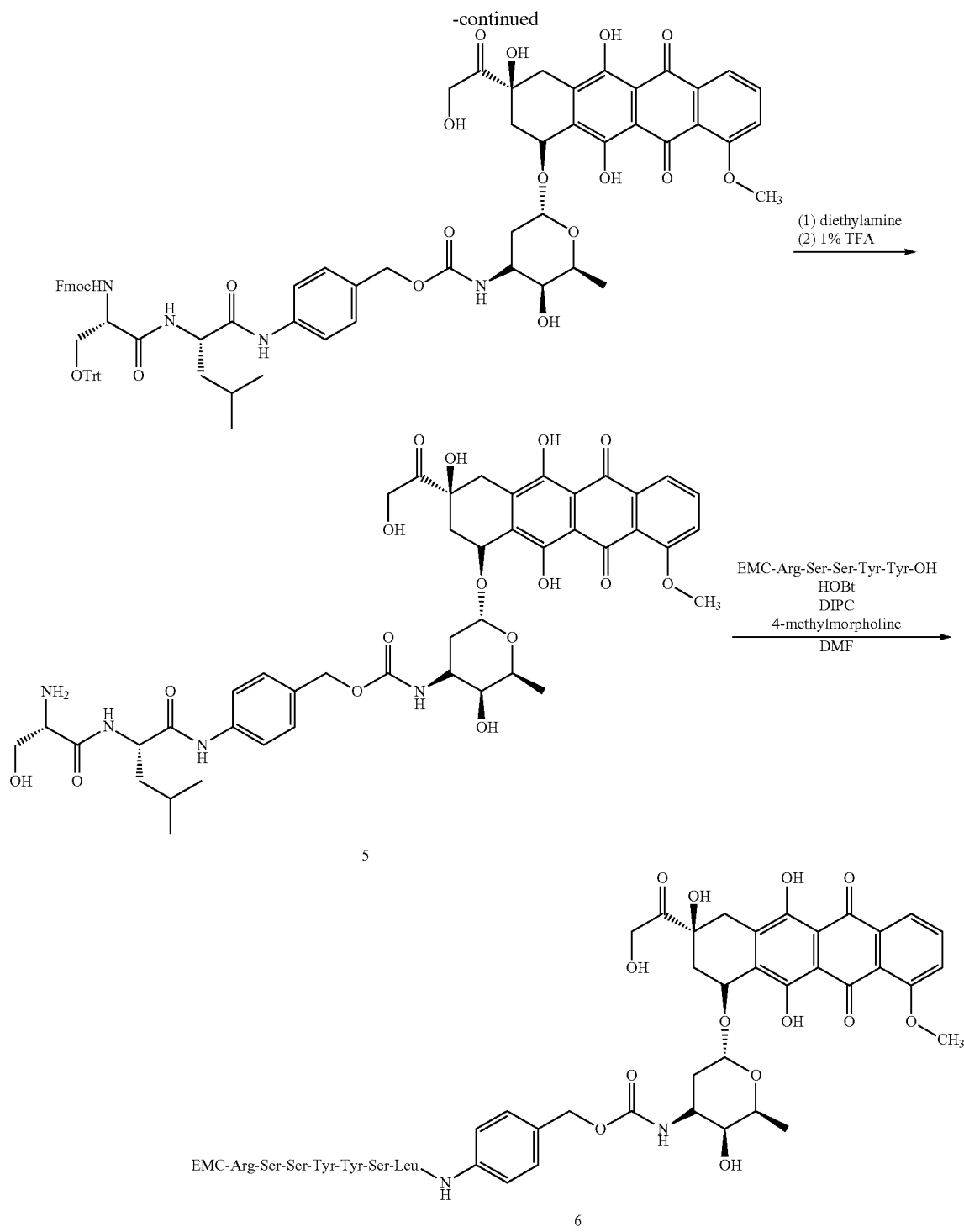

Synthesis of 6

Chemical Synthesis of the Paclitaxel Prodrug

Synthesis of Fmoc-Leu-PABC-PNP (7)

To a solution of 1 (0.70 g, 1.52 mmol) and bis(p-nitrophenyl)carbonate (2.32 g, 7.63 mmol) in anhydrous DMF (20 mL) at 0° C., DIEA (779 μL, 0.59 g, 4.57 mmol) was added and the reaction was stirred at room temperature for 48 hours. Subsequently, the volatiles were removed under reduced pressure, and the residue was purified on a silica gel column using chloroform/methanol (50:1) to afford 7 (800 mg, 84%) as a white powder. ESI-MS (5 kV, MeCN): m/z (%)=623.9 (100) [M+H]$^+$; HPLC (220 nm): >95%.

Synthesis of Fmoc-Leu-PABC-Paclitaxel (8)

Paclitaxel (0.37 g, 0.44 mmol) and 4-Dimethylaminopyridine (DMAP) (0.05 g, 0.44 mmol) were added to a solution of 7 (0.27 g, 0.44 mmol) in anhydrous DCM (15 mL), and the reaction was stirred in the dark at room temperature for 24 hours. Subsequently, DCM (20 mL) was added and the reaction mixture was extracted with $NaHCO_3$, brine and dried over sodium sulphate. The residue was purified on a silica gel column using ethyl acetate/hexane (1:1) to afford 8 (550 mg, 93%) as a white powder. ESI-MS (5 kV, MeOH): m/z (%)=1360.1 (100) $[M+Na]^+$; HPLC (230 nm): >95%.

Synthesis of H-Leu-PABC-Paclitaxel (9)

8 (0.50 g, 0.37 mmol) was treated with 1% of 1,8-Diazabi-cyclo[5.4.0]undec-7-en (DBU) in Tetrahydrofuran (THF) (10 mL) for 45 seconds at room temperature and the product was precipitated by 1 M HCl in diethyl ether (500 mL). Then it was purified on a silica gel column using chloroform/methanol (7:1) to afford 9 (350 mg, 84%) as a white powder. ESI-MS (5 kV, MeOH): m/z (%)=1116.1 (100) $[M+H]^+$; HPLC (230 nm): >95%.

Synthesis of EMC-Arg-Ser-Ser-Tyr-Tyr-Ser-Leu-PABC-Paclitaxel (10)

EMC-Arg-Ser-Ser-Tyr-Tyr-Ser-OH (84 mg, 88.68 µmol), 9 (90 mg, 80.61 µmol), HOBt (30 mg, 241.83 µmol) and 4-methylmorpholine (35 µL, 30 mg, 322.2 µmol) were dissolved in anhydrous DMF (10 mL). After stirring for 15 minutes at 0° C. DIPC (75 µL, 60 mg, 483.6 µmol) was added and the reaction was stirred at 5° C. for 72 hours. 10 was precipitated with diethyl ether (100 mL) and purified on a reverse-phase column using $CH_3CN$/water (40:60)+0.1% TFA to afford 10 (75 mg, 45%) as a white powder after lyophilizing the combined fractions containing the pure product. ESI-MS (3 kV, MeCN): m/z (%)=1027.2 (100) $[M/2+2H]^{2+}$; HPLC (230 nm): >95%.

Synthesis of Fmoc-Ser-Leu-PABC-Paclitaxel (11)

DIEA (15 µL, 0.011 g, 0.089 mmol) was added to a solution of Fmoc-Ser-OH (0.029 g, 0.089 mmol) and [2-(1H-9-azobenzotriazole-1-yl)-1,1,3,3-tetramethylaminium-hexafluoro phosphate] (HATU) (0.034 g, 0.089 mmol) in anhydrous DMF (3 mL). After stirring the reaction mixture at room temperature for 30 minutes 9 (0.1 g, 0.089 mmol) and DIEA (15 µL, 0.011 g, 0.089 mmol) were added and the reaction was stirred for 2 hours. Subsequently, the volatiles were removed under reduced pressure and the residue was purified on a silica gel column using ethyl acetate/hexane (2:1) to afford 11 (115 mg, 90%) as a white powder. ESI-MS (5 kV, MeOH): m/z (%)=1447.1 (100) $[M+Na]^+$; HPLC (230 nm): >95%.

Synthesis of H-Ser-Leu-PABC-Paclitaxel (12)

11 (0.1 g, 0.070 mmol) was treated with 1% DBU in THF (3 mL) for 45 seconds at room temperature and the product was precipitated by 1 M HCl in diethyl ether (200 mL) then it was purified on a silica gel column using chloroform/methanol (7:1) to afford 12 (75 mg, 89%) as a white powder. ESI-MS (5 kV, MeOH): m/z (%)=1225.1 (100) $[M+Na]^+$; HPLC (230 nm): >95%.

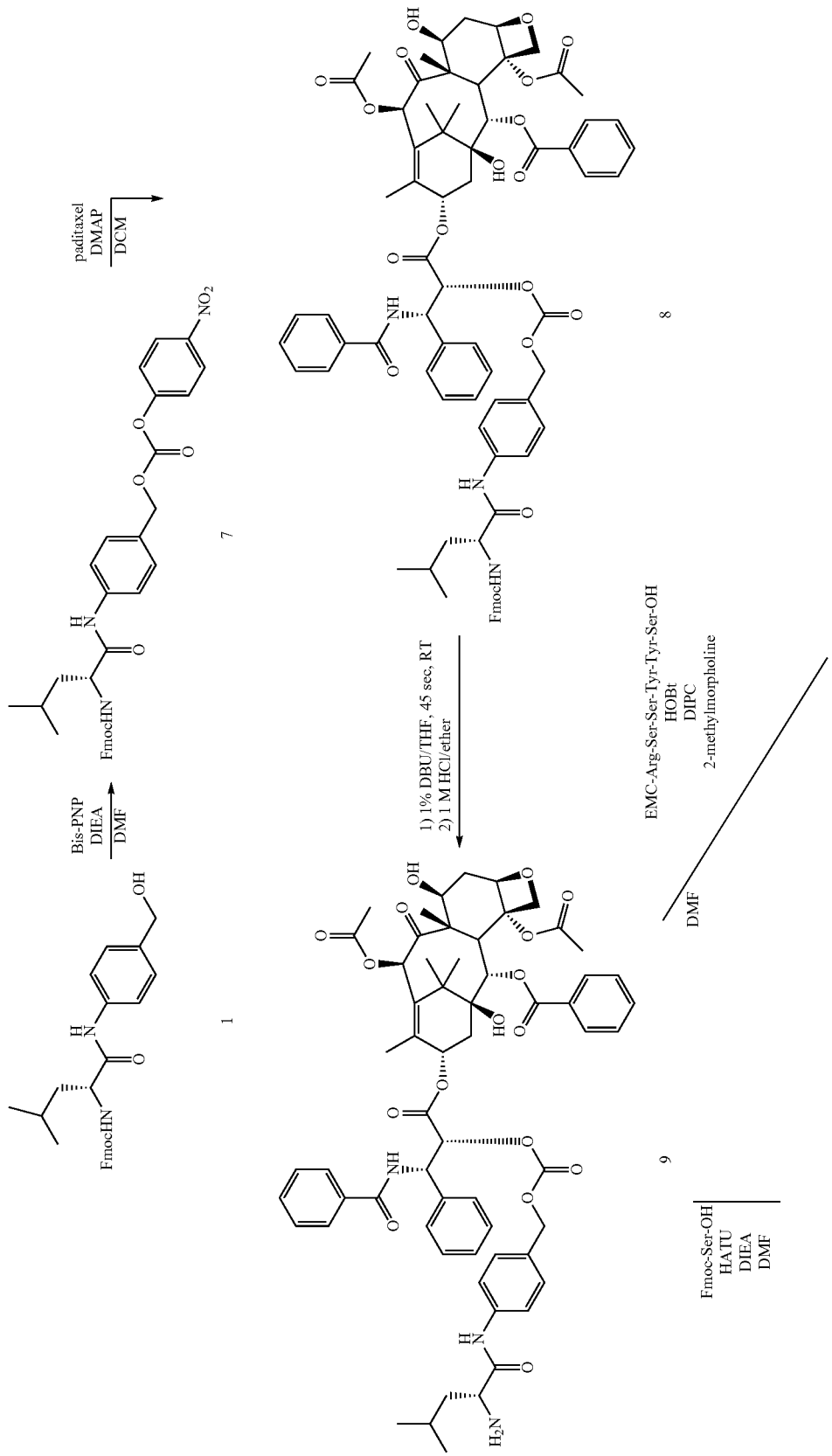

-continued
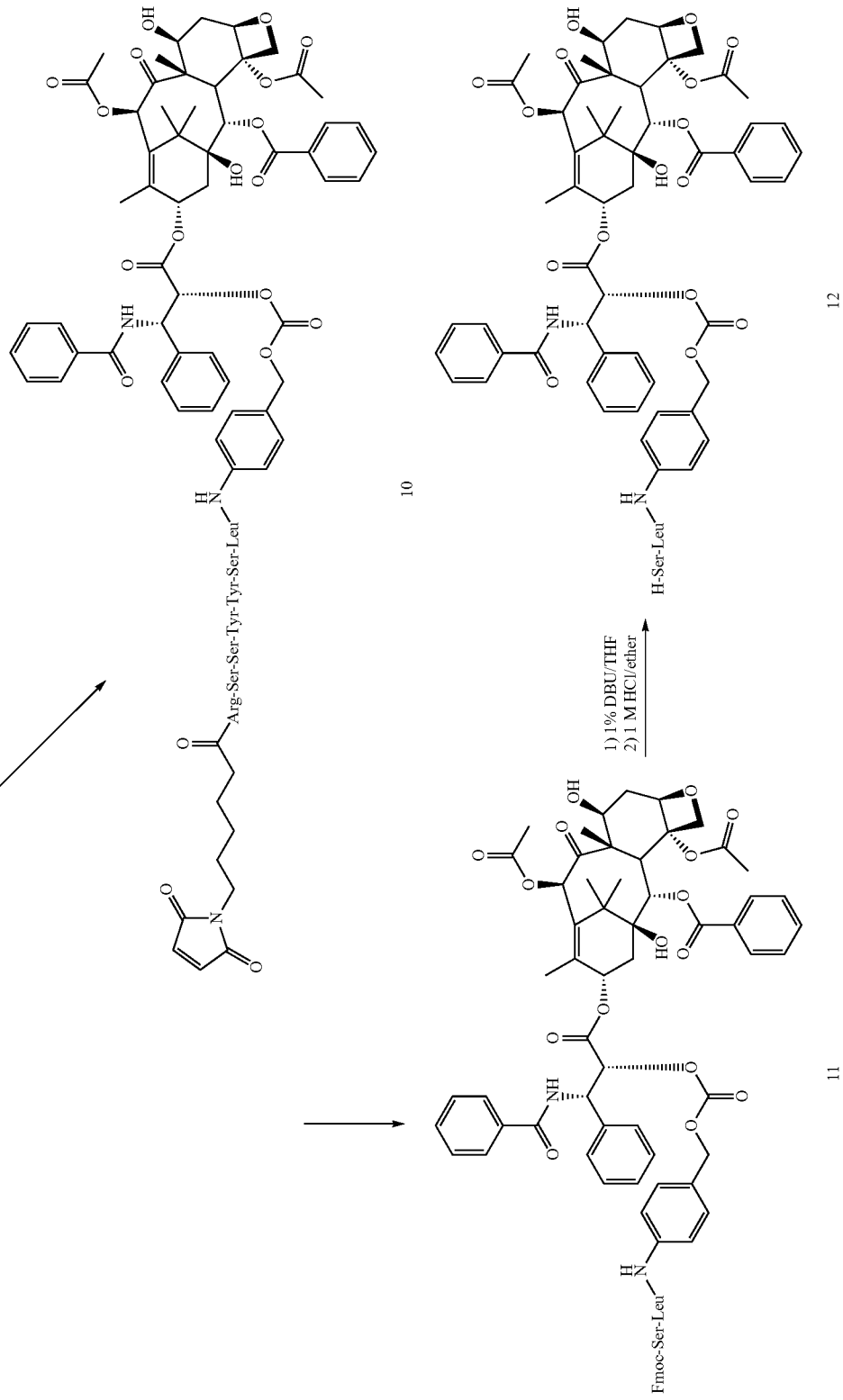

Synthesis of 10

Cleavage Studies of the Albumin-Bound Form of 6 and 10

Synthesis of the Albumin Conjugate of 6

The albumin conjugate was prepared by adding a solution of 6 [2 mg in 5% glucose solution (300 µL)] to human serum albumin (5% solution from Octapharma) (1700 µL). The mixture was incubated for 1 hour at 37° C. The albumin conjugate was obtained after subsequent size-exclusion chromatography (Sephacryl® S-100; 10 mM sodium phosphate buffer, pH 7.4). The content of anthracycline in the sample was determined using the ε-value for doxorubicin [$\epsilon_{495}$ (pH 7.4)=10650 $M^{-1}$ $cm^{-1}$]. The concentration of 6 in the conjugate was adjusted to 400±50 µM by concentrating the sample with CENTRIPREP®-10-concentrators (Amicon, Germany) at 4° C. and 4500 rpm. Samples were kept frozen at −20° C. and thawed prior to use.

Enzymatic Cleavage of the Albumin-Bound Form of 6 by PSA

The albumin-bound form of 6 (100 µM) was incubated with enzymatically active PSA (20 µg/mL) at 37° C. and the cleavage was monitored at different time points using HPLC (method B).

Cleavage of 5 by LNCaP Prostate Tumor Tissue Homogenates 5 (100 µM) was incubated with LNCaP prostate tumor tissue homogenates at 37° C. and the cleavage was monitored at different time points using HPLC (method B) using the following mobile phase; mobile phase A (30% $CH_3CN$, 70% water and 0.1% TFA), mobile phase B (70% $CH_3CN$, 30% water and 0.1% TFA).

Synthesis of the Albumin Conjugate of 10

The albumin conjugate of the prodrug was prepared by adding a solution of 10 [1 mg in 50 µL poly(ethylenglycol)-400+200 µL of 5% glucose solution] to human serum albumin (5% solution from Octapharma) at a final concentration of 300 µM and the mixture was incubated at 37° C. for 1 h. Samples were kept frozen at −20° C. and thawed prior to use.

Enzymatic Cleavage of the Albumin-Bound Form of 10 by PSA

The albumin-bound form of 10 (100 µM) was incubated with enzymatically active PSA (20 µg/mL) at 37° C. and the cleavage was monitored at different time points using HPLC (method C).

Cleavage of 12 by LNCaP Prostate Tumor Tissue Homogenates 12 (100 µM) was incubated with LNCaP prostate tumor tissue homogenates at 37° C. and the cleavage was monitored at different time points using HPLC (method C).

Cleavage Results

PSA-mediated cleavage of the albumin-bound form of both 6 and 10 revealed that the albumin-conjugates were cleaved efficiently within a few hours to liberate the doxorubicin-dipeptide (H-Ser-Leu-PABC-DOXO) or paclitaxel-dipeptide (H-Ser-Leu-PABC-paclitaxel) as shown in FIG. 1 and FIG. 2. Moreover, these drug-dipeptides showed a complete cleavage in the LNCaP prostate tumor tissue homogenates within ~3 hours liberating the free cytotoxic drug (doxorubicin or paclitaxel) as shown in FIG. 3 and FIG. 4. Incorporating the self-eliminating linker (PABC) between the peptide sequence and the active drug enhanced the cleavage rate. The reactions that are involved in the cleavage process are depicted in the following schemes:

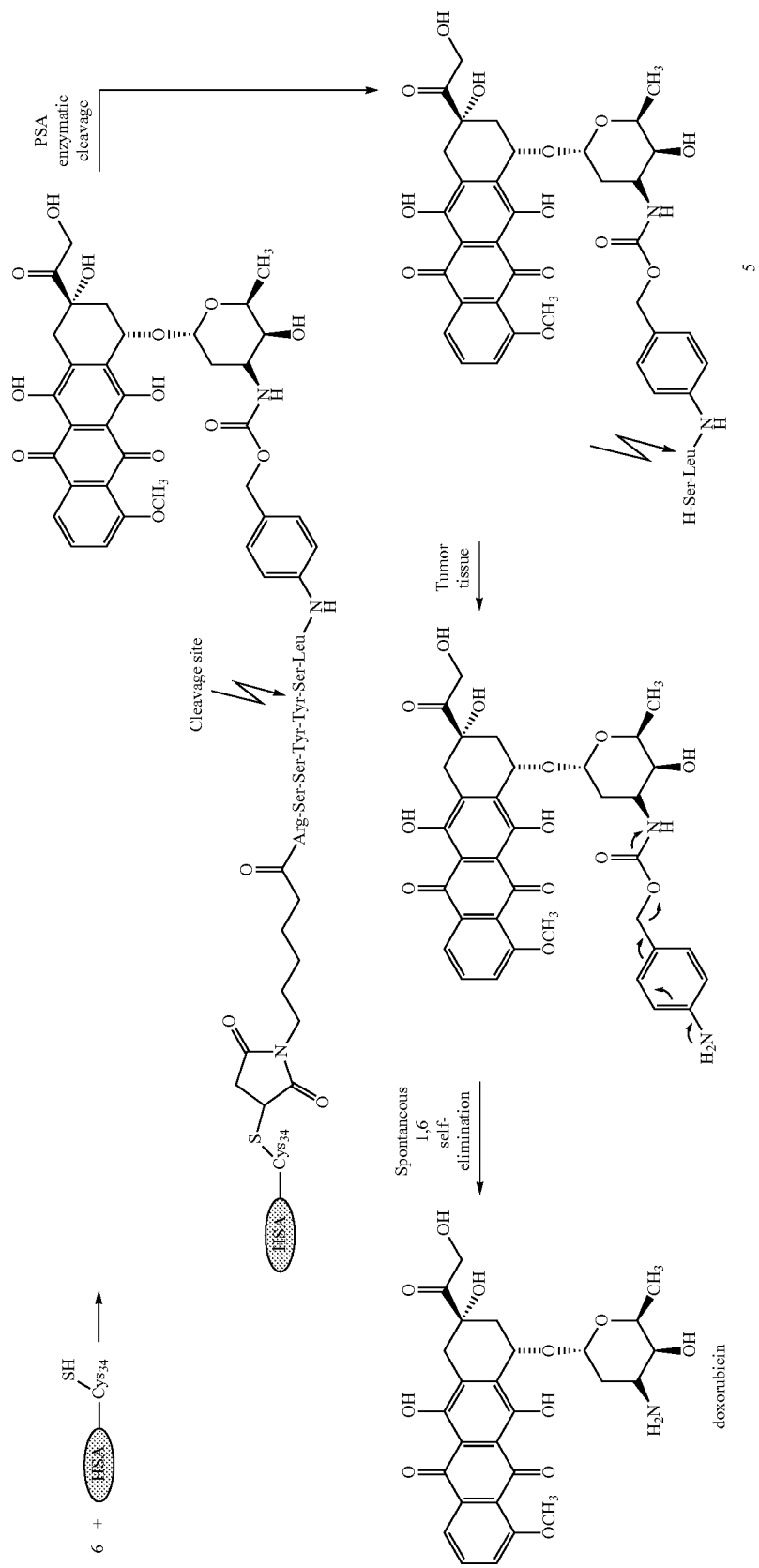

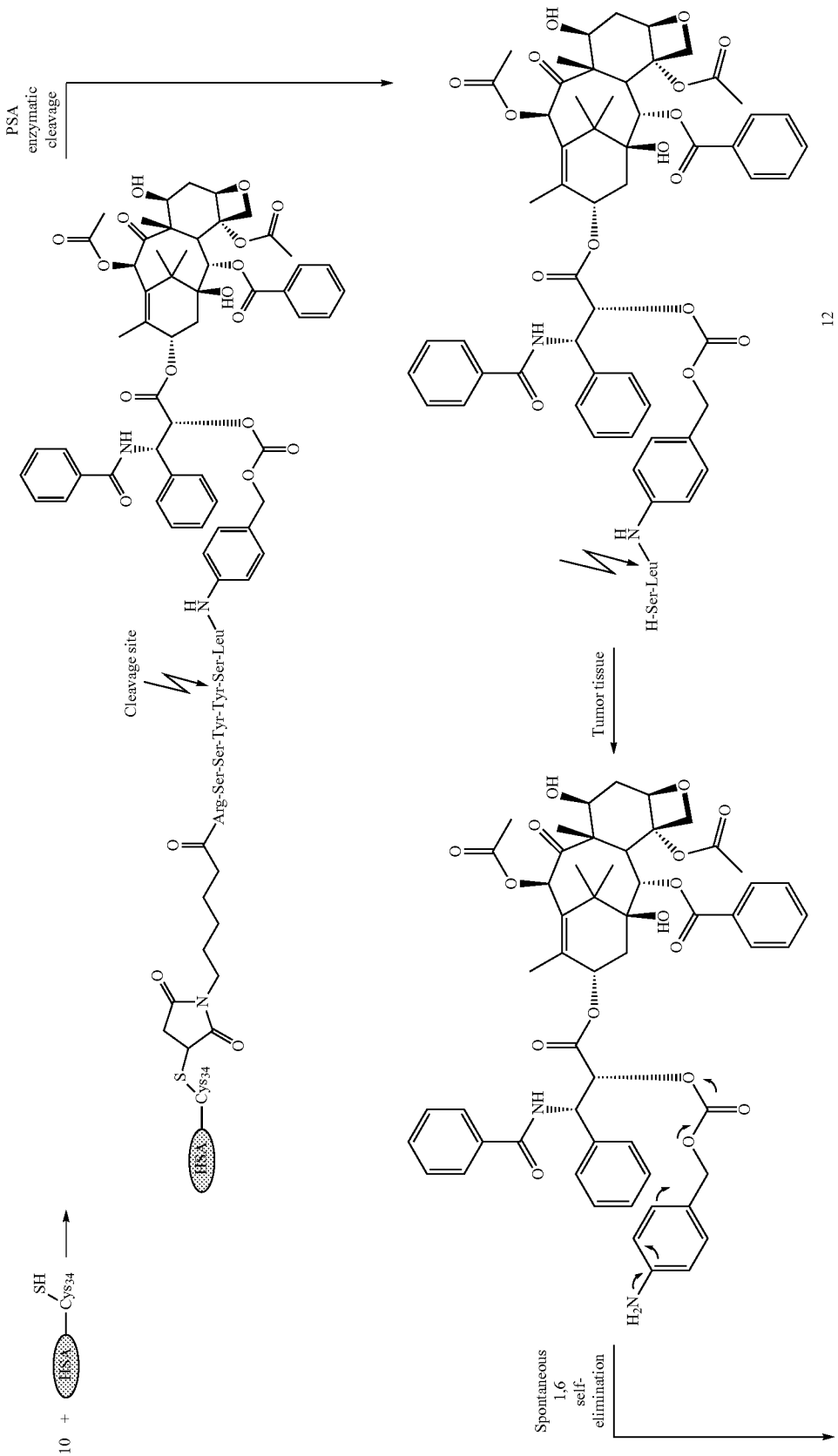

-continued
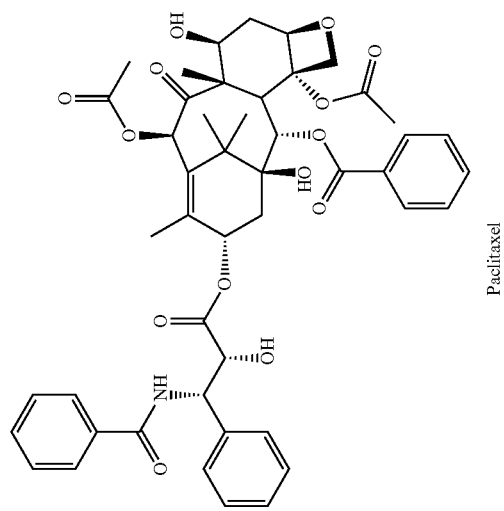
Paclitaxel

What is claimed is:

1. A prodrug having the following formula I:

$$R\text{-}A_n\text{-}Ser\text{-}Leu\text{-}Y\text{—}Z \qquad (I)$$

wherein

R = a protein binding moiety comprising a maleimide group and a $C_{1-10}$ acyl group;

A = a peptide sequence consisting of L- and/or D-amino acids, wherein the amino acid residues may be the same or different;

n = an integer from 1 to 10, indicating the number of amino acids in the peptide sequence;

Y = p-aminobenzyloxycarbonyl (PABC); and

Z = a cytostatic agent;

wherein the peptide sequence is selected from the group consisting of Arg-Ser-Ser-Tyr-Tyr (SEQ ID NO. 1), Arg-Ser-Ser-Tyr-Ser (SEQ ID NO. 2), Arg-Ser-Ser-Tyr-Arg (SEQ ID NO. 3), Ser-Ser-Tyr-Arg (SEQ ID NO. 4), Ser-Ser-Tyr-Tyr (SEQ ID NO. 5), Arg-Arg-Leu-His-Tyr (SEQ ID NO. 6), Arg-Arg-Leu-Asn-Tyr (SEQ ID NO. 7), Ser-Ser-Lys-Leu-Gln (SEQ ID NO. 8) and Arg-Ala-Ser-Tyr-Gln (SEQ ID NO. 9).

2. The prodrug according to claim 1, wherein R is ε-maleimidocaproic acid (EMC).

3. The prodrug according to claim 1, wherein the cytostatic agent is selected from the group consisting of N-nitrosoureas, anthracyclines, alkylating agents, antimetabolites, folic acid antagonists, camptothecins, Vinca alkaloids, taxanes, calicheamicins, maytansinoids, auristatins, epothilones, bleomycin, dactinomycin, plicamycin, mitomycin C and cis-configured platinum(ll) complexes.

4. The prodrug according to claim 1, having one of the following formulas:

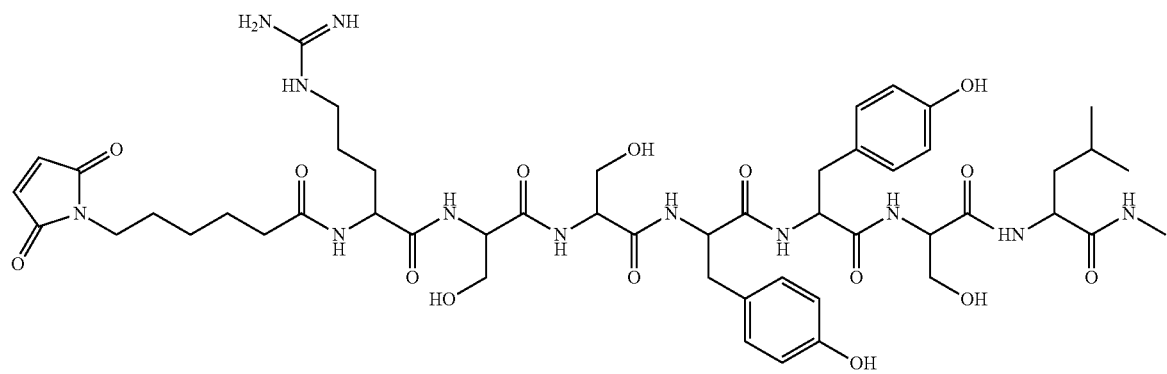
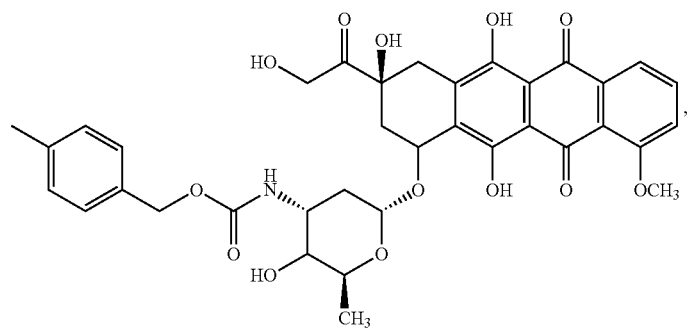
(=EMC-Art-Ser-Ser-Tyr-Tyr-Ser-Leu-PABC-doxorubicin)
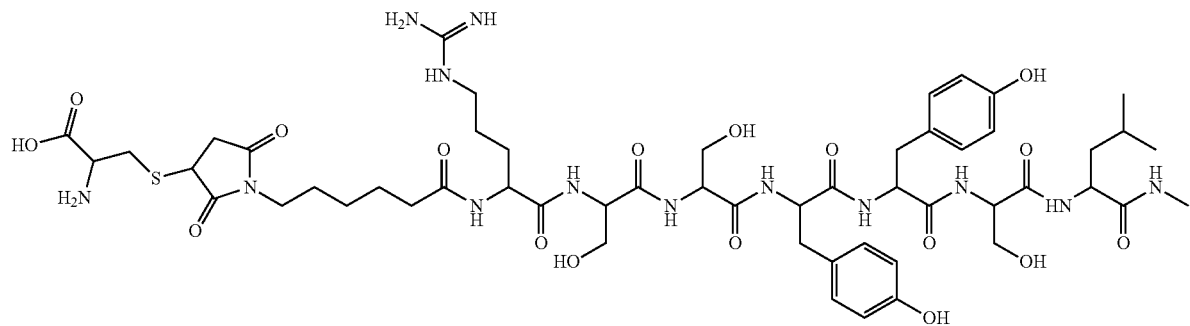
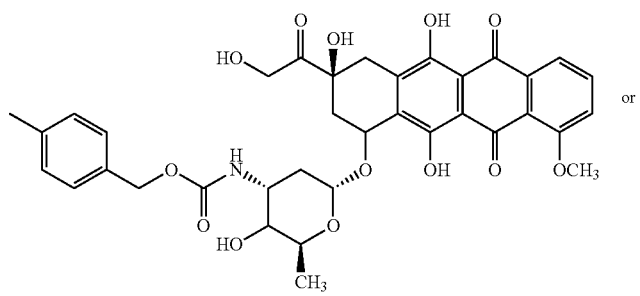
(Cys-EMC-Arg-Ser-Ser-Tyr-Tyr-Ser-Leu-PABC-doxorubicin)

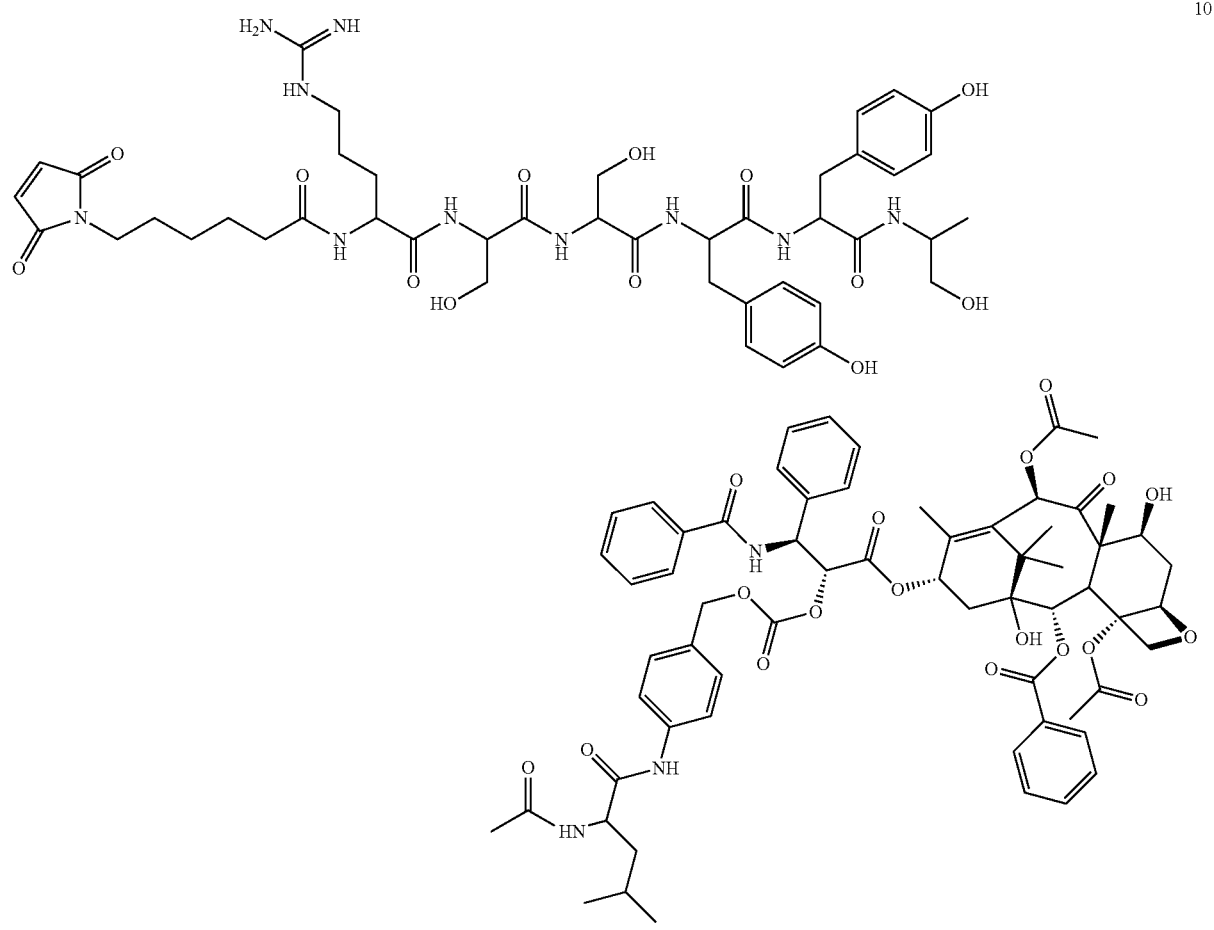

(=EMC-Arg-Ser-Ser-Tyr-Tyr-Ser-Leu-PABC-paclitaxel)

5. A process for the preparation of a compound as defined in claim 1, comprising the steps of reacting a compound having the formula II $$R\text{-}A_n \qquad (II)$$

with a compound having the formula III $$\text{Ser-Leu-Y—Z} \qquad (III)$$

wherein R, A, n, Y, and Z are as defined in claim 1.

6. A pharmaceutical composition containing the prodrug of claim 1 as a prodrug, and optionally a pharmaceutically acceptable carrier and/or diluent and/or adjuvant.

7. A method of treating prostate cancer comprising:
administering a pharmaceutical composition according to claim 6 to a subject in need of said treatment.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Prodrug sequence

<400> SEQUENCE: 1

Arg Ser Ser Tyr Tyr
 1               5

<210> SEQ ID NO 2
<211> LENGTH: 5
<212> TYPE: PRT
<213> ORGANISM: Artificial Sequence
<220> FEATURE:
<223> OTHER INFORMATION: Prodrug sequence

<400> SEQUENCE: 2

Arg Ser Ser Tyr Ser
 1               5

<210> SEQ ID NO 3
<211> LENGTH: 5
<212> TYPE: PRT
<213> ORGANISM: Artificial Sequence
<220> FEATURE:
<223> OTHER INFORMATION: Prodrug sequence

<400> SEQUENCE: 3

Arg Ser Ser Tyr Arg
 1               5

<210> SEQ ID NO 4
<211> LENGTH: 4
<212> TYPE: PRT
<213> ORGANISM: Artificial Sequence
<220> FEATURE:
<223> OTHER INFORMATION: Prodrug sequence

<400> SEQUENCE: 4

Ser Ser Tyr Arg
 1

<210> SEQ ID NO 5
<211> LENGTH: 4
<212> TYPE: PRT
<213> ORGANISM: Artificial Sequence
<220> FEATURE:
<223> OTHER INFORMATION: Prodrug sequence

<400> SEQUENCE: 5

Ser Ser Tyr Tyr
 1
```

```
<210> SEQ ID NO 6
<211> LENGTH: 5
<212> TYPE: PRT
<213> ORGANISM: Artificial Sequence
<220> FEATURE:
<223> OTHER INFORMATION: Prodrug sequence

<400> SEQUENCE: 6

Arg Arg Leu His Tyr
 1               5

<210> SEQ ID NO 7
<211> LENGTH: 5
<212> TYPE: PRT
<213> ORGANISM: Artificial Sequence
<220> FEATURE:
<223> OTHER INFORMATION: Prodrug sequence

<400> SEQUENCE: 7

Arg Arg Leu Asn Tyr
 1               5

<210> SEQ ID NO 8
<211> LENGTH: 5
<212> TYPE: PRT
<213> ORGANISM: Artificial Sequence
<220> FEATURE:
<223> OTHER INFORMATION: Prodrug sequence

<400> SEQUENCE: 8

Ser Ser Lys Leu Gln
 1               5

<210> SEQ ID NO 9
<211> LENGTH: 5
<212> TYPE: PRT
<213> ORGANISM: Artificial Sequence
<220> FEATURE:
<223> OTHER INFORMATION: Prodrug sequence

<400> SEQUENCE: 9

Arg Ala Ser Tyr Gln
 1               5
```